(12) United States Patent
Wexler

(10) Patent No.: US 6,238,413 B1
(45) Date of Patent: May 29, 2001

(54) APPARATUS FOR APPLYING CRANIAL OCCIPITAL PRESSURE

(76) Inventor: Robert Wexler, 4240 Navajo St., Toluca Lake, CA (US) 91602

( * ) Notice: Subject to any disclaimer, the term of this patent is extended or adjusted under 35 U.S.C. 154(b) by 0 days.

(21) Appl. No.: 09/109,911

(22) Filed: Jul. 2, 1998

(51) Int. Cl.[7] ........................................ A61F 5/08
(52) U.S. Cl. ........................................ 606/204.15
(58) Field of Search .................... 606/204, 191–203, 606/1; 601/134, 135; 607/110, 109, 108, 112; 2/12, 171, 426, 422, 425, 6.3, 312; 128/97.1; 602/74

(56) References Cited

U.S. PATENT DOCUMENTS

| | | | |
|---|---|---|---|
| 1,324,975 | * 12/1919 | Morris | 602/74 |
| 3,159,160 | * 12/1964 | Ullom | 128/97.1 |
| 4,606,077 | * 8/1986 | Phillips | 2/12 |
| 4,646,728 | * 3/1987 | Takeda | 128/97.1 |
| 4,716,898 | * 1/1988 | Chauve et al. | 606/204 |
| 4,944,289 | * 7/1990 | Matthews | 128/97.1 |
| 5,094,229 | 3/1992 | Pomatto et al. | 602/17 |
| 5,280,793 | 1/1994 | Rosenfeld . | |
| 5,405,311 | * 4/1995 | Pecora et al. | 601/135 |
| 5,419,758 | 5/1995 | Vijayan | 602/74 |
| 5,695,520 | * 12/1997 | Bruckner et al. | 606/204 |
| 5,737,777 | * 4/1998 | Hilleary | 2/421 |
| 5,848,981 | * 12/1998 | Herbranson | 601/134 |

* cited by examiner

Primary Examiner—Olik Chaudhuri
Assistant Examiner—Hoa B. Trinh
(74) Attorney, Agent, or Firm—Morgan, Lewis & Bockius LLP

(57) ABSTRACT

A mounting apparatus for applying pressure to the back of a human head having a harness for attaching the apparatus to the front portion of the head and a therapeutic pad attached to the harness. The therapeutic pad has a first and a second protrusion on an inner surface thereof, each adapted to contact an occiput at the back of the head.

3 Claims, 3 Drawing Sheets

APPARATUS FOR APPLYING CRANIAL OCCIPITAL PRESSURE

BACKGROUND OF THE INVENTION

1. Field Of The Invention

This invention relates to a headband or a fastening device for applying pressure to the back of a human head for therapeutic effects, and more particularly to a device that applies bilateral pressure to the occipital region to improve the circulation of cerebrospinal fluid.

2. Background Of The Invention

The human body is continually subjected to physical and other forms of stress that can stimulate the occurrence of a variety of ailments or otherwise cause detrimental effects to one's physical health or well-being. Physical stresses can include injuries stemming from birth trauma, automotive accidents, athletic exertions, or postural problems. Other forms of stress can occur from psychological tension or emotional disturbances, which may be caused by depression or anxiety. The occurrence of stress may manifest as muscle tension, which in turn may tighten the muscles around the head and neck. Severe or prolonged muscle tension in the area surrounding the cranium may distort the alignment of cranial bones.

Within the human cranium, cerebrospinal fluid fills the ventricles of the brain and occupies the subarachnoid space. The fluid is a clear watery fluid that remains in constant circulation throughout the brain and the spinal cord. The cerebrospinal fluid acts as both a protective cushion against injury and a carrier of nutrients and proteins that provide nourishment to the brain for normal functioning.

Cerebrospinal fluid drains from the lateral ventricles through the interventricular foramina of Monro into the third ventricle. This fluid then combines with that produced by the choroid plexus of the third ventricle, and then passes through the cerebral aqueduct of Sylvius into the fourth ventricle. The fluid escapes from the fourth ventricle through openings in its roof, the median foramen of Magendie and the two lateral foramina of Luschka. From the foramina of the fourth ventricle the fluid enters the subarachnoid space. Henry Gray and Charles Goss, *Gray's Anatomy*, Lea & Febiger, 1973.

There are four major rhythmic pulsations from fluid circulation within the cranium. Blood flows from cardiovascular circulation between 60 to 72 times per minute to provide circulation throughout the brain and the entire body. Oxygen is provided to the vascular system through respiratory circulation at 14 to 19 times per minute. There is also a sutural pulsations at 14 to 19 times per minute and dural pulsations movement at 6 to 8 times per minute, which are measured as a cranial rhythm index. These rhythmic pulsations affect the circulation of cerebrospinal fluid.

With regard to fourth rhythmic pulsation, this flexion/extension movement provides tension changes to the membrane, within the dural system. Dural flexion occurs when the distance from the internal margin of the lamboid and the superior posterior margin of the sphenobasilar articulation decreases in distance. This decrease in distance produces a slight tension to the external margin of the falx cerebrum, falx cerebullum, and the falx tentorium. The internal margin of the membrane produces a slight relaxation of the falx cerebrum, falx cerebellum, and the falx tentorium. This membrane tension change allows the external cisterns and superior sagital sinus to decrease in volume and size. When this takes place, the ventricles of the brain increase in volume and size. The cerebrospinal fluid moves with the fluctuations of this rhythmic cycle.

If the skeletal structure in the cranium is improperly aligned, it is possible that the cerebrospinal fluid cannot provide optimal circulation throughout the cerebrum. By applying pressure to the cranium, it is possible to stimulate greater circulation to reverse, or at least reduce the harmful effects of suboptimal cerebrospinal fluid flow. In 1939, Dr. William Garner Sutherland, DO, experimented with a technique of applying pressure to the occipital region of the head to cause a compression of the fourth ventricle, adjacent to the cerebellum. Traditionally called a "CV-4" technique, a therapist presses against the occiput and to apply resistance against movement to modify the activity of the craniosacral system. This can induce a "still-point" that can enhance the flow of cerebrospinal fluid throughout the cerebrum. Upon reaching a "still-point," a patient can enjoy a sense of relaxation.

A subject must remain immobile in order to induce a "still point." Thus, previous methods or devices for inducing relaxation by applying pressure to the occipital region require the assistance of a therapist, or devices that require a patient to remain immobile while receiving treatment. The inconvenience of relying upon another to provide treatment and remaining in a still position during a treatment process greatly reduces the benefits of the treatment and limits the opportunities for achieving a state of relaxation from the application of occipital pressure.

SUMMARY OF THE INVENTION

Accordingly, the present invention is directed to an apparatus for applying occipital pressure that substantially obviates one or more problems and limitations in the prior art.

It is an object of the present invention to provide an apparatus for relieving muscular tension around the head.

It is another object of the present invention to provide a device for affecting the intracranial hydraulic pressure and its circulation throughout the dural membrane system within the cerebrum.

It is yet another object of the present invention to provide a portable, mobile, and unobtrusive device for self-treatment of pain or discomfort by applying soothing pressure on the back of the head.

Additional features and advantages of the invention will be set forth in the description which follows and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a mounting apparatus for applying pressure to the back of a human head, comprising a harness for attachment to the front portion of the head and a therapeutic pad having two ends, attached at the ends to the harness, where the therapeutic pad has two protrusions on an inner surface, such that each protrusion is adapted to contact the occiput at the back of the head.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incor- In the drawings.

DESCRIPTION OF THE PREFERRED EMBODIMENTS

Reference will now be made in detail to the preferred embodiments of the present invention, examples of which are illustrated in the accompanying drawings. Certain terminology is used in the following description to facilitate the description only and is not intended to be limiting in its use.

Figure 1:
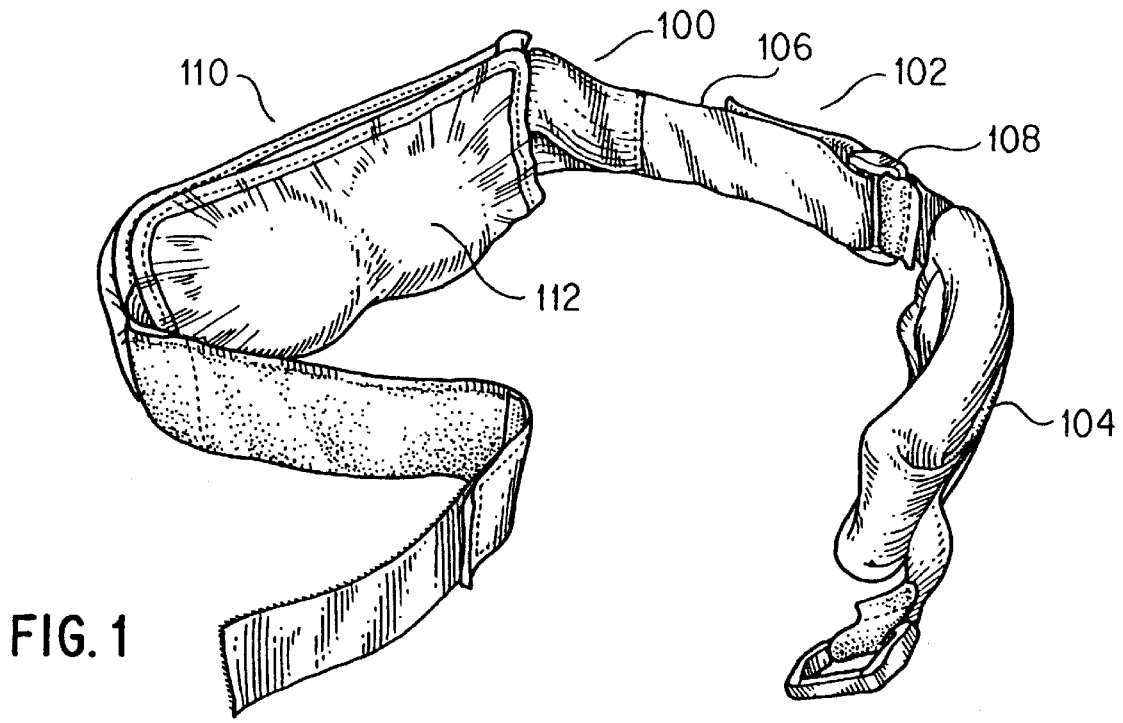
FIG. 1 shows a perspective view of an apparatus for applying cranial occipital pressure.

The present invention is comprised of a mounting apparatus for applying pressure to the back of the human head, including a harness and a therapeutic pad. Referring to the drawings in detail, wherein like numerals indicate like elements throughout, FIG. 1 shows a preferred embodiment of a headband 100 in accordance with the present invention. The headband shown in FIG. 1 is intended to be an example of the many types of headbands and other related devices for applying occipital pressure. In particular, the headband in FIG. 1 has a harness that preferably comprises a band 102 connected to a forehead pad 104. The preferred band 102 includes a strap 106 and a buckle 108. The strap 106 interlinks within the buckle 108 to form the band 102 that connects the forehead pad 104 to a therapeutic pad 110. In the preferred embodiment according to FIG. 1, there is a second band composed of a second strap and a second buckle for forming a symmetrical harness attached to the therapeutic pad 110. The strap 106 may be made be secured about the buckle 108 when worn on a head by a hook and loop fastener on the outer strap surface disposed away from the head. The strap may be made of other materials, such as leather or cotton, and may be secured by other means, such as by buttons or snaps, sufficient to fasten the therapeutic pad 110 about the back of the head. Discussion will now be directed to the therapeutic pad 110.

The preferred therapeutic pad 110 is configured to apply bilateral pressure at the back of the head when worn. The therapeutic pad 110 can be made of any material suitable for maintaining a force against the head, including nylon, rayon, cotton, leather, etc. As shown in FIG. 1, the therapeutic pad 110 is sewn closed around the sides and an upper portion and contains an inner material shaped to form two protrusions 112 appearing along the inner surface. The prousions are symmetrical about the center of the pad to apply the desired bilateral pressure when worn.

Figure 2:
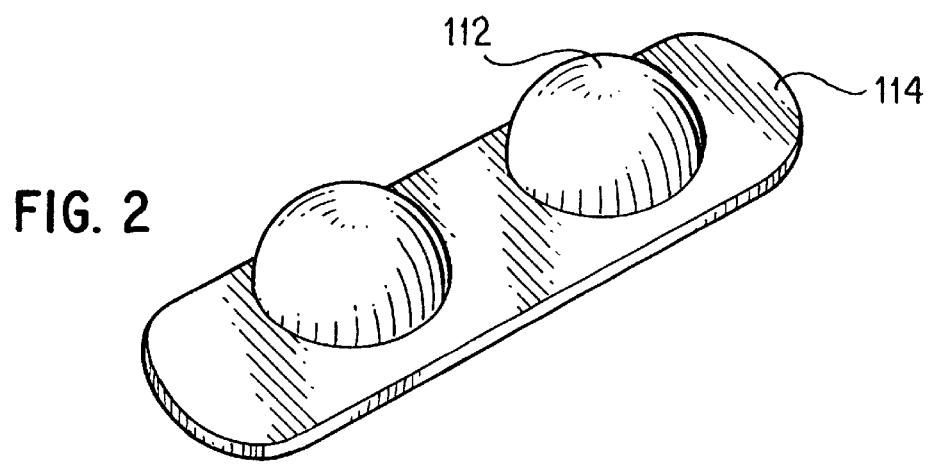
FIG. 2 shows a top view of an apparatus for applying cranial occipital pressure worn on a head.

FIG. 2 provides a top view of a preferred embodiment of the headband when worn. The forehead pad 104 has a benefit of providing cushioning to the forehead to facilitate the comfort when wearing the mounting apparatus. The forehead pad 104 additionally positions the therapeutic pad on the cranium such that the force is received at the proper angle and placement at the occiput. FIG. 2 provides an illustration of how the theaptic pad contacts the occiput. The force upon which the protrusions are applied to the occiput is depenent upon the adjustment of each band 102. In FIG. 2, the directional force of pressure applied onto the occiput in relation to the primary cranial bones is shown. Although the headband in FIG. 2 contacts the cranium about the sides, it is conceivable that the therapeutic pad 110 can be of sufficient width such that, when the band is attached about the ends of the pad, the bands do not contact the head when worn.

Figure 3A:
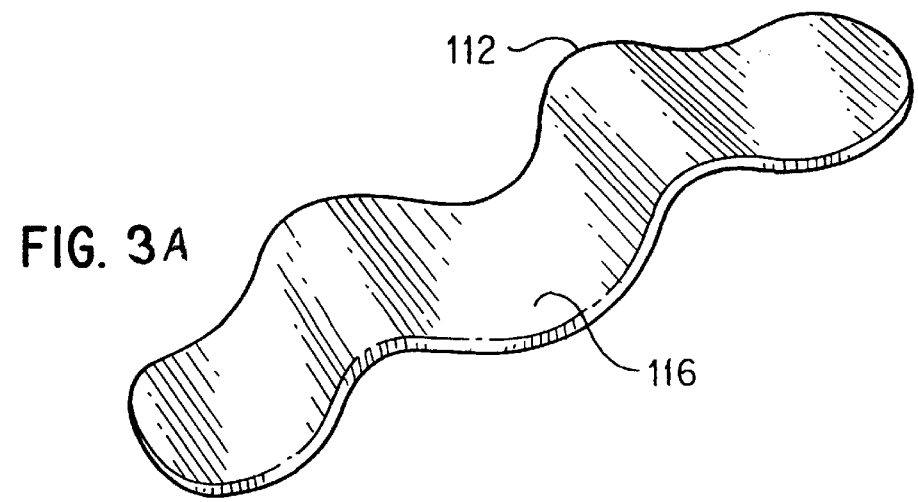
FIG. 3A shows a view of a plate with attached protrusions for applying occipital pressure.

The two protrusions 112 are caused by two generally semispherical objects placed within the therapeutic pad 110. The spheres can be made of rubber, foam, metal, plastic, or any other material sufficient to apply pressure against the occiput. The spheres can also be filled with a fluid that be heated or chilled. In FIG. 3A, the two protrusions 112 (semi-spheres) are connected through an attachment plate 114 that is placed within the pad 110. The spheres can also be sewn directly into the pad 110 (not shown), or connected through a plate metal of metal, plastic, cloth, etc.

Figure 3B:
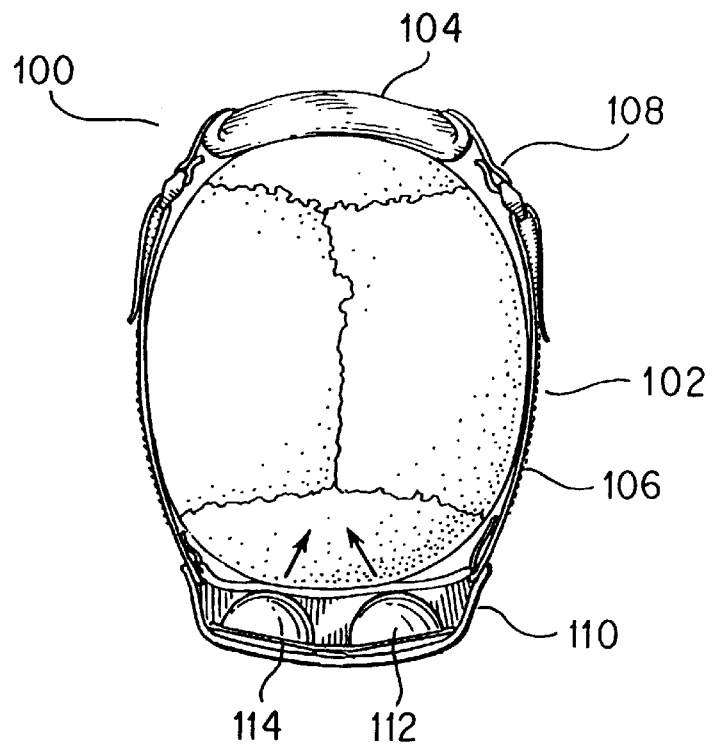
FIG. 3B shows a view of a curvilinear plate with integrated protrusions for applying occipital pressure.

In an alternative embodiment, the protrusions 112 can be formed within the therapeutic pad 110 by a single curved structure, such as a piece of metal formed to provide the symmetrical protrusions. FIG. 3B illustrates a curved portion 116 that serves to apply bi-lateral pressure to the occiput. The curved portion 116 can be sewn directly into the pad 110 (not shown).

Figure 4:
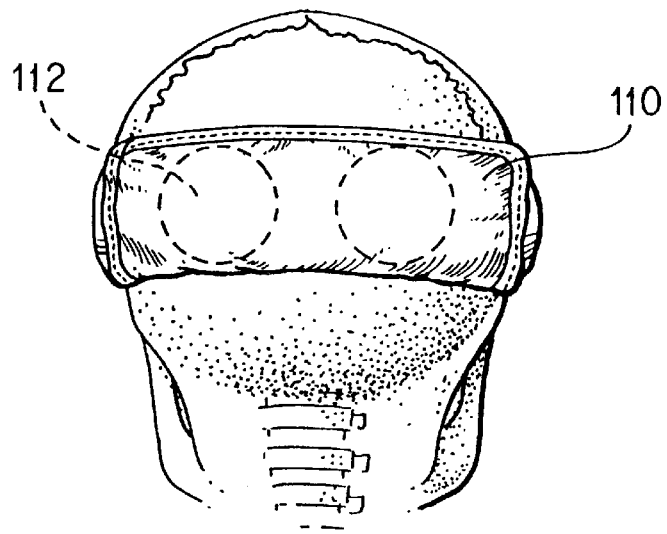
FIG. 4 shows a rear view of an apparatus for applying cranial occipital pressure with hidden lines illustrating protrusions.

FIG. 4 illustrates a rear view of the mounting apparatus of the headband of the preferred embodiment. The two protrusions 112 are shown with hidden lines in order to illustrate the proper positioning of the mounting apparatus about the occiput. In accordance with this invention, the two protrusions 112 should be equi-distant from the midline to the right and to the left on the occiput. The protrusions 112 should be superior to the external occiptal nucal ridge, and inferior to the lamboidal suture.

Figure 5:
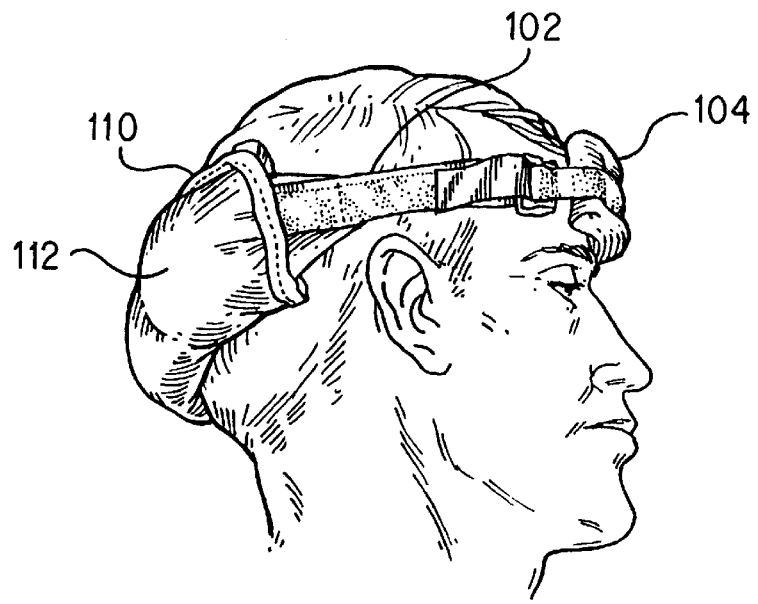
FIG. 5 illustrates a profile view of an apparatus for applying cranial pressure worn on a head.

FIG. 5 illustrates a perspective view of the mounting apparatus of the headband of the preferred embodiment to illustrate the proper positioning of the mounting apparatus. As shown in FIG. 5, the mounting apparatus can be worn while standing, sitting, or exercising. In accordance with the invention, the forehead pad 104 should be slightly superior to the frontal eminence. The resulting effective pressure upon the head should be approximately one to five pounds.

With the mounting apparatus properly in place, a constant pressure is exerted against the occiput, applying resistance against the dural rhythmic pulsations. The wearer can then experience a relaxing, therepeutic effect while remaining mobile and capable of continuing normal, daily activities.

Figure 6:
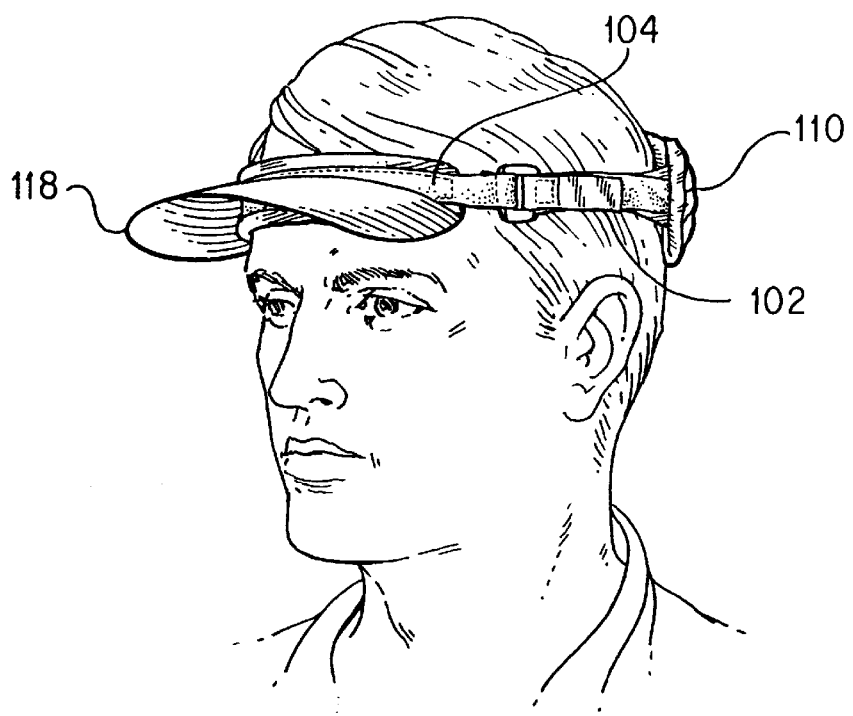
FIG. 6 illustrates a profile view of an apparatus for applying cranial pressure with a sun visor worn on a head.

It will be apparent to those skilled in the art that various modifications and variations can be made in the headband without departing from the spirit or scope of the invention. For example, the harness can include a visor attached about the front to cover or shade the face while wearing the apparatus. As illustrated in FIG. 6, a bill 118 is attached to the outer surface of the forehead pad 104.

A variety of other designs and modifications can aid to make the device more fashionable or comfortable while still applying occipital pressure. In another alternative embodiment, the therapeutic pad can be attached to the occiput by means of a hat or a cap, which serves to cover the head and disguise the apparatus from public view. The cap can be further equipped with a front visor to shade the face, much like a conventional baseball cap. As can be readily understood, the hat or cap would include a harness as part of its structure for holding the therapeutic pad against the occiput. This hat or cap can be modified from a conventional baseball cap to further include side straps for adjusting the size of the cap for different head sizes or different desired tension levels at the sides of the cap. In accordance with the invention, a hat or cap can be modified to provide the bilateral occipital pressure in accordance with the invention by inserting therapeutic padding within the inner portion of the back of the cap to apply bilateral occipital pressure. The back padding can be temporarily inserted and attachable to the inner portion of the cap by Velcro hook-and-loop fasteners. If a curvilinear insert as shown in FIG. 2B is inserted to the rear portion of a cap, the pressure points for applying occipital pressure can be adjusted by bending the curvilinear structure.

When the mounting apparatus as shown in FIGS. 1–6 is worn, it will be appreciated that the applied bilateral occipital pressure puts the cranium in a state of flexion. In an alternative embodiment, two and/or alternate additional pressure points can be applied to the frontal bone in the cranium to enhance the relaxing and therapeutic effects induced by applying occipital pressure. In particular, by supplementing the mounting apparatus with two protrusions on the harness, the wearer can benefit from bilateral frontal compression. Optional removable pads can be added to the inside of a front cushion, or a front portion of a visor or hat to apply bilateral frontal pressure as desired. The frontal pads can be attached (glued or sewn) onto a removable hook-and-loop Velcro strap that can be affixed to the inner side of the forehead cushion 104. Alternatively, the frontal pads can be directly attached to the inner side of the forehead cushion 104 by Velcro attachments. The frontal pads are removable because it may not be desirable in some cases to apply both frontal and occipital pressures.

It is also possible to wear the mounting apparatus as shown in FIG. 5 in reverse, such that bilateral pressure is applied to the frontal bone, and lateral, uniform pressure is applied to the occiput. It is intended that the present invention cover the modifications and variations of this invention provided they come within the scope of the appended claims and their equivalents.

I claim:

1. A mounting apparatus for applying pressure to the back of a human head, comprising:

a harness for attachment to the front portion of the head; and a therapeutic pad having first and second ends attached to the harness, the therapeutic pad also having first and second protrusions spaced a distance apart and adapted to apply equal bilateral pressure to an occiput at the back of the head, the first and second protrusions being formed from inside the therapeutic pad by two semi-spheres.

2. A mounting apparatus for applying pressure to the back of a human head, comprising:

a harness for attachment to the front portion of the head; and a therapeutic pad having first and second ends attached to the harness, the therapeutic pad also having first and second protrusions spaced a distance apart and adapted to apply equal bilateral pressure to an occiput at the back of the head, the first and second protrusions being formed from inside the therapeutic pad by a single curved structure.

3. A mounting apparatus for applying pressure to the back of a human head, comprising:

means for applying pressure to an occiput, the pressure means including protruding means for applying bilateral pressure about the occiput, and the protruding means including two semi-spheres; and a harnessing means connected to the pressure means for attachment to the head.

\* \* \* \* \*